US008679179B2

(12) United States Patent
Ferree

(10) Patent No.: US 8,679,179 B2
(45) Date of Patent: Mar. 25, 2014

(54) ANNULAR REPAIR DEVICES AND METHODS

(75) Inventor: Bret A. Ferree, Cincinnati, OH (US)

(73) Assignee: Anova Corp., Summit, NJ (US)

( * ) Notice: Subject to any disclaimer, the term of this patent is extended or adjusted under 35 U.S.C. 154(b) by 1362 days.

(21) Appl. No.: 12/030,706

(22) Filed: Feb. 13, 2008

(65) Prior Publication Data

US 2008/0140126 A1    Jun. 12, 2008

Related U.S. Application Data

(63) Continuation of application No. 10/264,157, filed on Oct. 3, 2002, now abandoned.

(51) Int. Cl.
*A61F 2/44* (2006.01)
(52) U.S. Cl.
USPC ..................... 623/17.11; 623/17.16
(58) Field of Classification Search
USPC ....................................... 623/17.11
See application file for complete search history.

(56) References Cited

U.S. PATENT DOCUMENTS

| | | | |
|---|---|---|---|
| 4,413,359 A | 11/1983 | Akiyama | |
| 4,512,338 A | 4/1985 | Balko | |
| 4,663,358 A | 5/1987 | Hyon | |
| 4,743,256 A | 5/1988 | Brantigan | |
| 4,772,287 A | 9/1988 | Ray | |
| 4,834,757 A | 5/1989 | Brantigan | |
| 4,904,260 A | 2/1990 | Ray | |
| 4,932,969 A | 6/1990 | Frey | |
| 5,015,255 A | 5/1991 | Kuslich | |
| 5,047,055 A | 9/1991 | Bao | |
| 5,059,193 A | 10/1991 | Kuslich | |
| 5,100,422 A | 3/1992 | Berguer | |
| 5,123,926 A | 6/1992 | Pisharodi | |
| 5,147,374 A | 9/1992 | Fernandez | |
| 5,171,278 A | 12/1992 | Pisharodi | |
| 5,192,326 A | 3/1993 | Bao | |
| 5,258,043 A | 11/1993 | Stone | |
| 5,304,194 A | 4/1994 | Chee | |
| 5,334,217 A | 8/1994 | Das | |
| 5,342,394 A | 8/1994 | Matsuno | |
| 5,370,660 A | 12/1994 | Weinstein | |
| 5,390,683 A | 2/1995 | Pisharodi | |
| 5,425,744 A | 6/1995 | Fagan | |
| 5,425,772 A | 6/1995 | Brantigan | |

(Continued)

FOREIGN PATENT DOCUMENTS

| | | | |
|---|---|---|---|
| WO | WO 01/28464 | 4/2001 | |
| WO | WO 02/058599 A2 * | 8/2002 | ............... A61F 2/44 |

*Primary Examiner* — Paul Prebilic
(74) *Attorney, Agent, or Firm* — Pandiscio & Pandiscio

(57) ABSTRACT

Methods and devices are described for occluding openings in an annulus fibrosis to prevent conditions such as disc herniation and recurrent disc herniation. An occluding device having an intradiscal component, an extradiscal component, and a barrier element disposed between the intradiscal and extradiscal components is provided. The intradiscal component has first and second arms having a collapsed state with a horizontal dimension less than the width of the opening and an expanded state having a horizontal dimension greater than the width of the opening. The barrier element and the intradiscal component in the collapsed state are inserted through the annulus fibrosis opening, the extradiscal component being positioned adjacent an outer surface of the annulus fibrosis. The intradiscal component assumes the expanded state in the intradiscal space, the first and second arms urging the barrier element against the inner wall of the annulus fibrosis adjacent the opening, thereby occluding the opening.

12 Claims, 12 Drawing Sheets

(56) References Cited

U.S. PATENT DOCUMENTS

| | | |
|---|---|---|
| 5,451,235 A | 9/1995 | Lock |
| 5,496,318 A | 3/1996 | Howland |
| 5,540,715 A | 7/1996 | Katsaros |
| 5,545,229 A | 8/1996 | Parsons |
| 5,562,736 A | 10/1996 | Ray |
| 5,571,189 A | 11/1996 | Kuslich |
| 5,634,944 A | 6/1997 | Magram |
| 5,645,597 A | 7/1997 | Krapiva |
| 5,649,950 A | 7/1997 | Bourne |
| 5,681,310 A | 10/1997 | Yuan |
| 5,709,707 A | 1/1998 | Lock |
| 5,716,416 A | 2/1998 | Lin |
| 5,741,297 A | 4/1998 | Simon |
| 5,800,549 A | 9/1998 | Bao |
| 5,800,550 A | 9/1998 | Sertich |
| 5,824,093 A | 10/1998 | Ray |
| 5,827,328 A | 10/1998 | Buttermann |
| 5,879,366 A | 3/1999 | Shaw |
| 5,916,225 A | 6/1999 | Kugel |
| 5,976,174 A | 11/1999 | Ruiz |
| 5,976,186 A | 11/1999 | Bao |
| 6,007,570 A | 12/1999 | Sharkey |
| 6,024,754 A | 2/2000 | Engelson |
| 6,132,465 A | 10/2000 | Ray |
| 6,224,630 B1 | 5/2001 | Bao |
| 6,245,107 B1 * | 6/2001 | Ferree .................. 606/279 |
| 6,264,695 B1 * | 7/2001 | Stoy .................... 623/17.16 |
| 6,425,919 B1 | 7/2002 | Lambrecht |
| 6,592,625 B2 * | 7/2003 | Cauthen ............... 623/17.16 |
| 6,656,206 B2 | 12/2003 | Corcoran |
| 2002/0189622 A1 | 12/2002 | Cauthen |
| 2004/0002763 A1 * | 1/2004 | Phillips et al. ....... 623/17.16 |
| 2005/0197702 A1 * | 9/2005 | Coppes et al. ....... 623/17.12 |

\* cited by examiner

ANNULAR REPAIR DEVICES AND METHODS

REFERENCE TO RELATED APPLICATIONS

This application is a continuation of U.S. application Ser. No. 10/264,157, filed Oct. 3, 2002 now abandoned. This application is also related to U.S. patent application Ser. No. 09/807,820, which is the U.S. national phase of PCT application Serial No. PCT/US00/14708, filed May 30, 2000, which claims priority from U.S. patent application Ser. No. 09/322,516, filed May 28, 1999, now U.S. Pat. No. 6,245,107. The entire content of each of the above-referenced applications are herein expressly incorporated by reference in their entirety.

FIELD OF THE INVENTION

This invention relates generally to prosthetics and, in particular, to devices for occluding intervertebral disc defects and instrumentation associated with the introduction of such devices.

BACKGROUND OF THE INVENTION

Several hundred thousand patients undergo disc operations each year. Approximately five percent of these patients will suffer recurrent disc herniation, which results from a void or defect which remains in the outer layer (annulus fibrosis) of the disc after surgery involving partial discectomy.

In the disc of a healthy patient, the nucleus pulposus is entirely surrounded by the annulus fibrosis. In the case of the herniated disc, a portion of the nucleus pulposus has ruptured through a defect in the annulus fibrosis, often resulting in a pinched nerve. This results in pain and further complications, in many cases.

One accepted treatment involves a partial discectomy. Following such a procedure, a void remains adjacent a hole or defect in the annulus fibrosis following removal of the disc material. This hole may act as a pathway for additional material to protrude into the nerve, resulting in the recurrence of the herniation.

I have devised various solutions to this condition. Reference is made to my U.S. Pat. No. 6,245,107, the entire content of which is incorporated herein by reference, the subject matter of which resides in methods and apparatus for treating disc herniation, and recurrent disc herniation, in particular.

To correct defects of this type, a conformable device is provided which assumes a first shape associated with insertion and a second shape or expanded shape to occlude the defect. The device may take different forms according to the invention, including solidifying gels or other liquids or semi-liquids, patches sized to cover the defect, or plugs adapted to fill the defect.

The device is preferably collapsible into some form for the purposes of insertion, thereby minimizing the size of the requisite incision while avoiding delicate surrounding nerves. Such a configuration also permits the use of instrumentation to install the device, including, for example, a hollow tube and a push rod to expel the device or liquefied material out of the sheath for use in occluding the disc defect.

A device according to the invention may further include one or more anchors to assist in permanently affixing the device with respect to the defect. For example, in the embodiment of a mesh screen, the anchors may assume the form of peripheral hooks configured to engage with the vertebra on either side of the disc. The teachings further contemplates a distracting tool used to force the anchors into the vertebra. Such a tool would preferably feature a distal head portion conformal to the expanded shape of the device, enabling the surgeon to exert force on the overall structure, thereby setting the anchors.

SUMMARY OF THE INVENTION

This invention is broadly directed to devices for occluding defects in an annulus fibrosis to prevent conditions such as disc herniation and recurrent disc herniation. Assuming the defect has a width and height, and given that the annulus fibrosis has an inner surface defining an intradiscal space between adjacent vertebrae separated by an intervertebral spacing, the preferred embodiments comprise an intradiscal component having a width greater than the width of the defect and a height less than the intervertebral spacing, and an extradiscal component physically coupled to the intradiscal component, the extradiscal component having a height greater than the intervertebral spacing.

In the most preferred embodiment the intradiscal component comprises two outwardly extending arms. The extradiscal component also preferably comprises two outwardly extending arms, these being generally transverse to the arms of the intradiscal component. The arms of the intradiscal component may be of equal or unequal length, and the arms extradiscal component are of sufficient length to overlap at least a respective portion of the adjacent vertebrae.

The intradiscal component is typically positioned adjacent the inner surface of the annulus fibrosis, with the invention further including a body disposed between the intradiscal and extradiscal components to at least partially consume the defect. The body is composed of a natural or synthetic biocompatible material, such as a resilient or compressible natural or synthetic rubber, allograft tendon, or other suitable substances. A barrier element, such as a mesh or compressible layer, or strengthening member, may further be disposed between the intradiscal component and the inner surface of the annulus fibrosis. Optionally as well, a biasing element such as a spring or tensioning cable may be inserted between the intradiscal and extradiscal components to urge them toward one another.

In terms of an inventive method, one or both of the intradiscal and extradiscal components may articulate or otherwise temporarily collapse to facilitate a compressed introduction into the intradiscal space. The method includes a step for occluding an opening in the annulus fibrosis of an intervertebral disc. The opening has a width and a height, and the annulus fibrosis has an outer surface and an inner surface defining an intradiscal space between adjacent vertebrae separated by an intervertebral spacing. The intradiscal component includes first and second arms extending along a first axis and terminating in opposing ends. The opposing ends of the first and second arms define a first dimension greater than the width of the opening. The extradiscal component has third and fourth arms extending along a second axis and terminating in opposing ends, the second axis extending perpendicularly to the first axis. The opposing ends of the third and fourth arms define a second dimension greater than the intervertebral spacing. The method involves inserting the intradiscal component and the barrier element through the opening in the annulus fibrosis and into the intradiscal space, with the extradiscal component being positioned adjacent the outer surface of the annulus fibrosis and making a sliding engagement with at least one of the adjacent vertebrae. The occluding device is oriented so that the first axis is disposed horizontally across the width of the opening and the second axis is disposed vertically across the height of the opening, and with the first and second arms of the intradiscal component urging the barrier element against the inner wall of the annulus fibrosis adjacent the opening to occlude the opening.

DETAILED DESCRIPTION OF THE INVENTION

This invention resides in an annular repair device (ARD) used to prevent recurrent disc herniation as well as the extrusion of artificial disc replacements. Very broadly, the device resembles an oversized plastic connector of the type used to hold tags on clothes at department stores. The preferred embodiment includes two sets of arms oriented 90 degrees from one another. The first set of arms rests on the inside of the Annulus Fibrosis. The second set of arms rests behind the vertebrae. The device can be made of metal, plastic, rubber, and/or suitable tissue such as allograft tendon.

Figure 1:
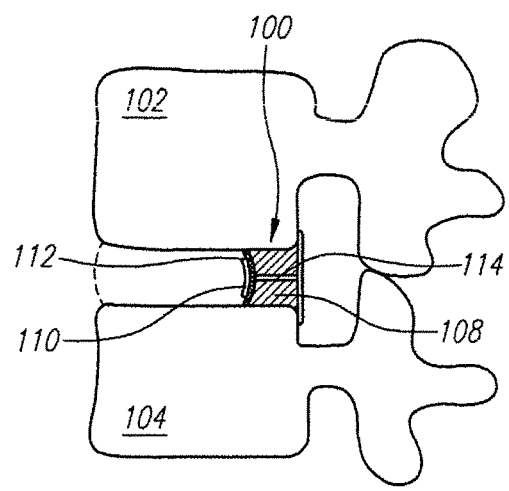
FIG. 1 is a lateral view of the spine and a device according to a preferred embodiment of the invention.
Figure 2:
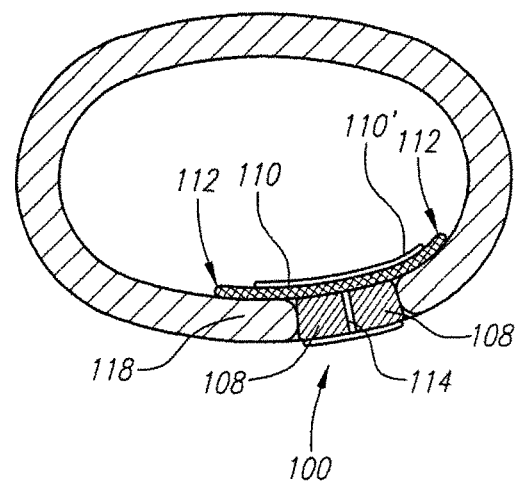
FIG. 2 is an axial cross section of the disc with the device of FIG. 1 in position.
Figure 3:
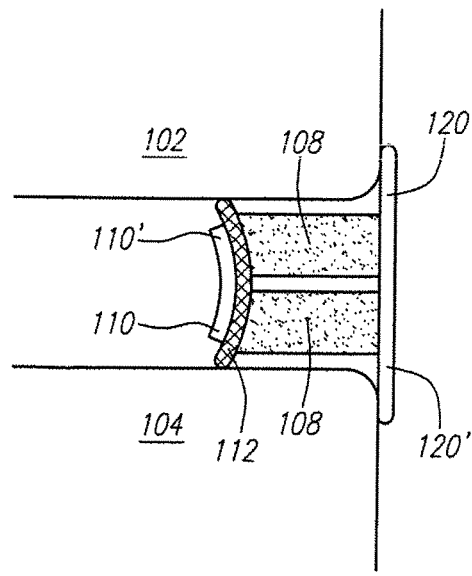
FIG. 3 is an enlarged lateral view of the device and a portion of the vertebrae.
Figure 4:
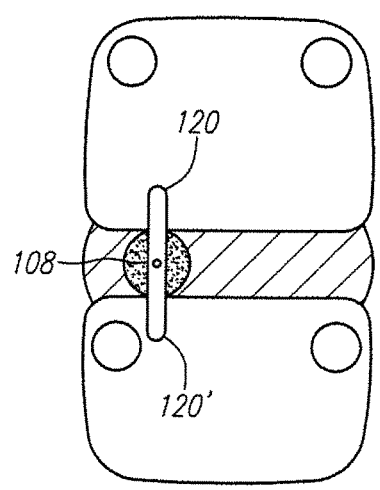
FIG. 4 is a view of the anterior aspect of the spinal canal with the posterior elements of the vertebrae removed to better view the device.
Figure 5A:
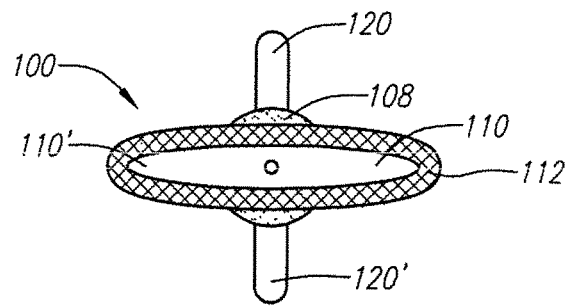
FIG. 5A is a view of the device from an intradiscal perspective.
Figure 5B:
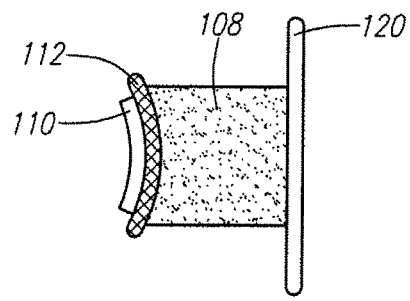
FIG. 5B is a view of the lateral aspect of the device.
Figure 5C:
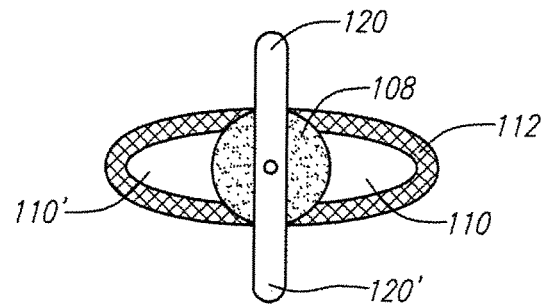
FIG. 5C is a view of the device viewed the spinal canal side.

FIG. 1 is a lateral view of the spine and a device 100 according to a preferred embodiment of the invention. FIG. 2 is an axial cross section of the disc with the device 100 in position. FIG. 3 is an enlarged lateral view of the device and a portion of the vertebrae 102, 104. FIG. 4 is a view of the anterior aspect of the spinal canal with the posterior elements of the vertebrae removed to better view the device. FIG. 5A is a view of the device 100 as seen from an intradiscal perspective. FIG. 5B is a view of the lateral aspect of the device, and FIG. 5C is a view of the device from the spinal canal side.

In these figures, the diagonally hatched area 108 represents a cylinder-shaped piece of natural or synthetic material, preferably rubber or allograft tendon. Allograft tendon may aid tissue ingrowth into the device. Note that the device is not attached to either vertebra. Instead, arms 110, 110' inside the disc are used to hold a mesh or dam 112 against the inner surface of the annulus 118, being held in position by the inner set of arms. The cylinder 108 fills the hole in the annulus. The inner arms 110, 110' are narrow enough to allow the vertebrae 102, 104 to come closer together with spinal compression or spinal extension. The mesh or dam 112 is compressible to allow spinal motion yet prevent the extrusion of small pieces of disc material.

A connector portion 114 of the device connects the two sets of arms 110, 110'. The connector portion 114 is surrounded by the rubber or allograrft cylinder 108. The connector portion 114 is coupled to a second set of arms 120, 120', best seen in FIGS. 3, 4 and 5 which rest on the posterior aspect of the vertebral bodies. In the preferred embodiment, the geometry of the connector portion 114 bows the two sets of arms toward the connector, as perhaps best seen in FIG. 2. Thus, one set of arms pulls on the other set of arms to prevent migration of the device while the vertebrae are free to move. The arms within the spinal canal are long enough to remain positioned behind the vertebrae with distraction of the posterior portion of the vertebrae during spinal flexion.

Figure 6:
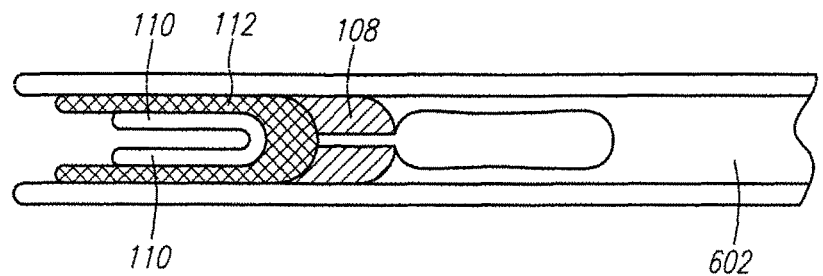
FIG. 6 is a view of the collapsed device positioned within a tube ready for insertion.
Figure 7A:
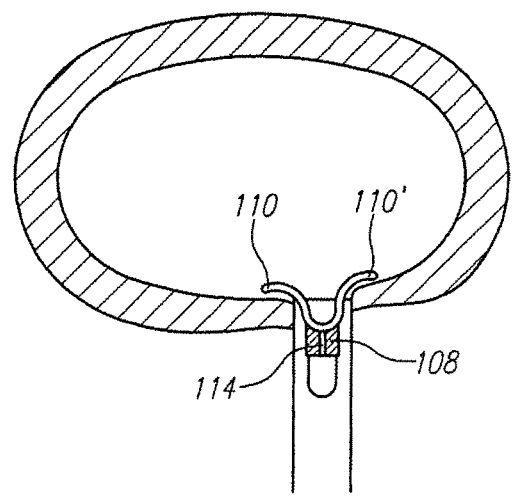
FIG. 7A is an axial view of the device in the first stage of insertion.
Figure 7B:
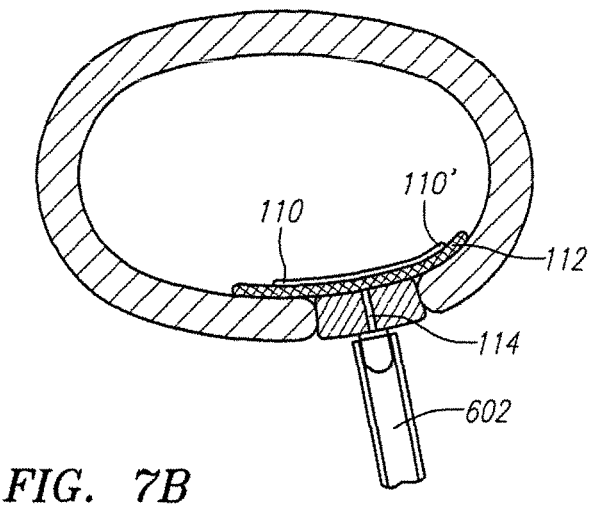
FIG. 7B shows the second stage of insertion.
Figure 7C:
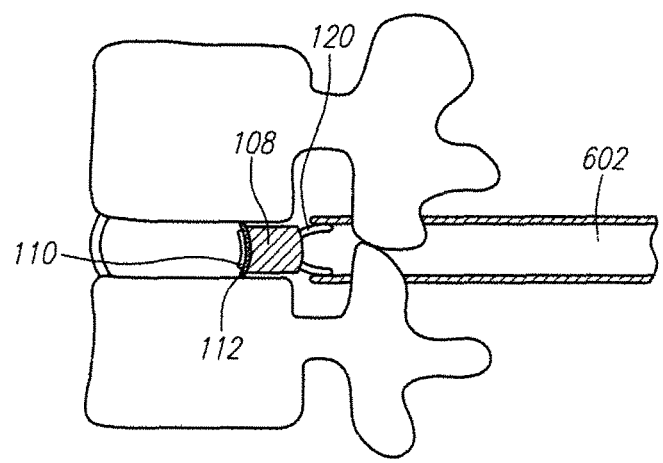
FIG. 7C is a lateral view of the spine and device at the same stage of insertion as shown in FIG. 7B.
Figure 7D:
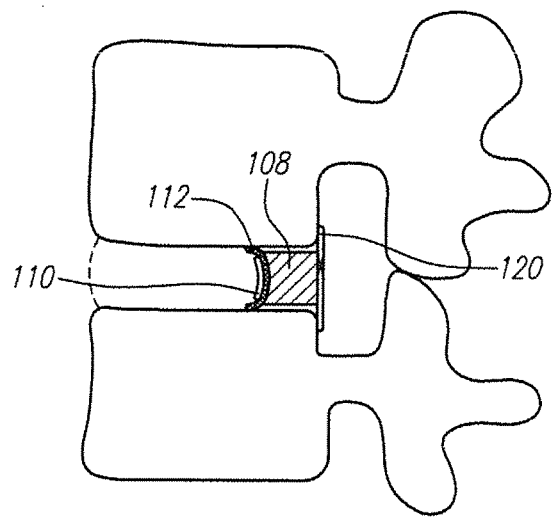
FIG. 7D is a lateral view of the spine with the both sets of arms fully deployed.

The device is constructed for introduction through a relatively small incision. FIG. 6 shows the collapsed device positioned within a tube 602. Note how the intradiscal arms 110, 110' may extend the opposite direction of the collapsed spinal canal arms. FIG. 7A is an axial view of the device in the first stage of insertion, wherein the intradiscal arms extend as the device is pushed from the tube. FIG. 7B shows the second stage of insertion, with the intradiscal arms are now fully deployed. The spinal canal arms 120, 102' are still collapsed, however. FIG. 7C is a lateral view of the spine and device at the same stage of insertion as that depicted in FIG. 7B. FIG. 7D is a lateral view of the spine with the both sets of arms fully deployed.

Figure 8:
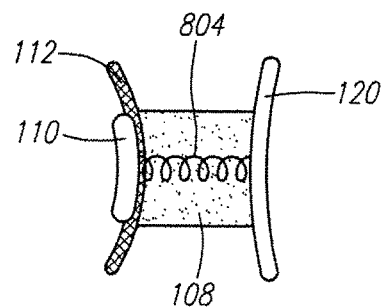
FIG. 8 shows an alternative embodiment of the invention in the form of a device with arms connected by a spring.
Figure 9A:
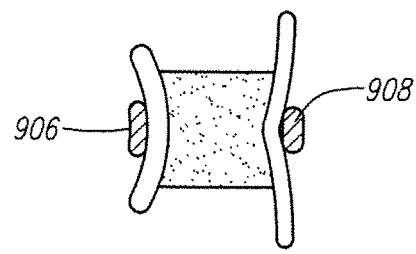
FIG. 9A is a drawing of an alternative device having the two sets of arms of the device are oriented 90 degrees to one another.
Figure 9B:
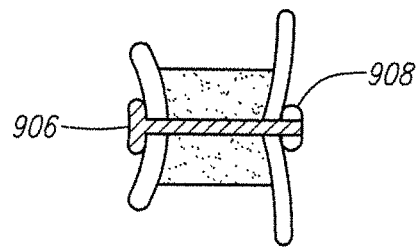
FIG. 9B is a cross section of the device drawn in FIG. 9A.

FIG. 8 shows an alternative embodiment of the device, wherein arms are interconnected with a biasing element such as a spring 804. As in the other embodiments, the embodiment of FIGS. 9A and 9B includes two sets of arms generally oriented 90 degrees to one another. FIG. 9B is a cross section of the device drawn in FIG. 9A, with the dotted area represents a component, preferably compressible, that lies within the annular hole to prevent the device from sliding up or down on the back of the vertebral bodies.

The hatched area 906 represents an elongated component or cable that extends through both sets of arms and the compressible center component. Tension is applied to the longitudinal component bowing both sets of arms. A crimp 908 on the longitudinal component holds the tension on the arms of the device.

Figure 10:
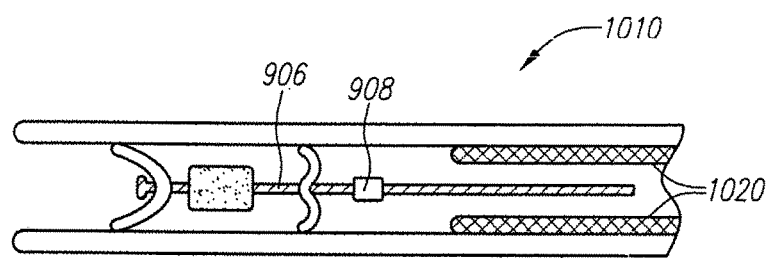
FIG. 10 is a cross section of a tool loaded with the device of FIGS. 9A and 9B.
Figure 11:
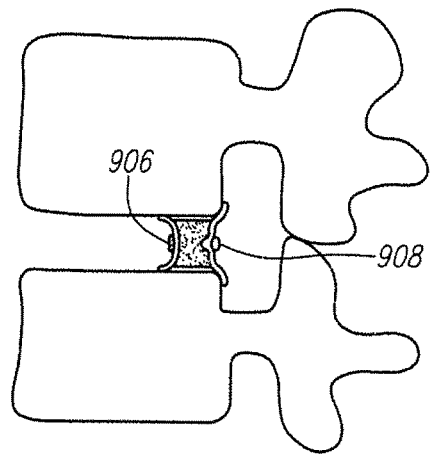
FIG. 11 is a sagittal view of the spine and a device according to the invention.

FIG. 10 is a cross section of a tool 1010 loaded with the device of FIG. 9. The area 1020 represents a portion of the tool that pushes the device out of the tool. A second portion of the tool (not drawn) pulls on the elongated component or cable. Once a sufficient amount of tension is obtained, a component of the tool deforms the crimp and cuts the longitudinal component. FIG. 11 is a sagittal view of the spine with the device of FIGS. 9 and 10 in position.

Figure 12:
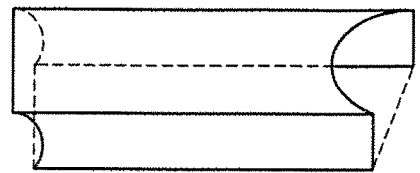
FIG. 12 illustrates yet a further alternative embodiment of a device having a compressible center component.

FIG. 12 is a view of an alternative embodiment wherein a central component features arms that cooperate with the sides of the arms of the longitudinal component within spinal canal. The arms of the center component would help prevent rotation of the longitudinal component within the spinal canal. Thus, the arms of the center component would keep the longitudinal component positioned behind the vertebrae.

Figure 13:
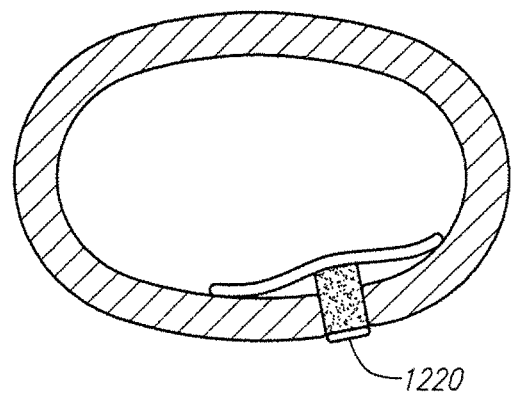
FIG. 13 is a view of a different embodiment of an intradiscal component according to the invention.
Figure 14:
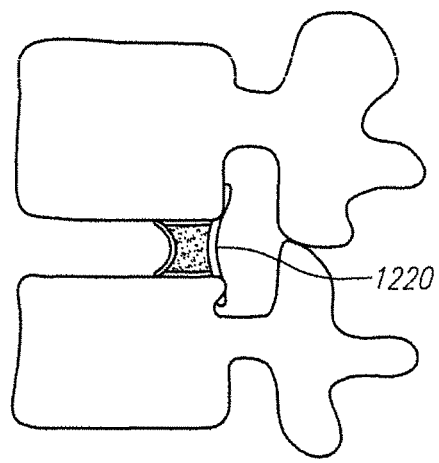
FIG. 14 shows how a longitudinal component may be recessed into the back of the vertebrae to help prevent impingement of the device on the nerves within the spinal canal.

FIG. 13 is a view of an alternative embodiment of the intradiscal component of FIG. 12. Such an intradiscal component could be convex to help deflect disc material. FIG. 14 is a lateral view of the spine and the device of FIGS. 12 and 13. Note that in this and in other embodiments the longitudinal component 1220 could be recessed into the back of the vertebrae to help prevent impingement of the device on the nerves within the spinal canal.

Figure 15A:
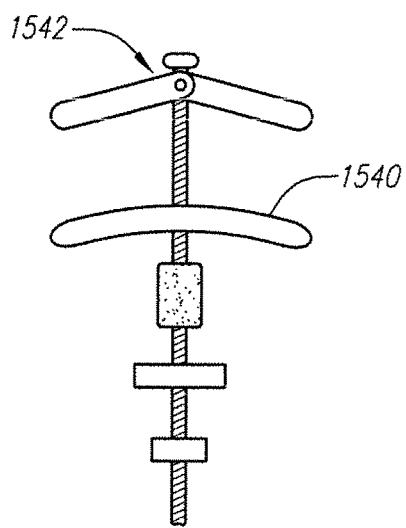
FIG. 15A shows a spring-loaded "toggle bolt" type component used within the disc space.
Figure 15B:
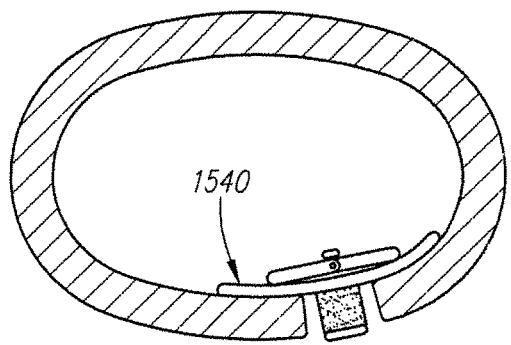
FIG. 15B is a view of the device of FIG. 15A positioned within the disc space.

FIG. 15A shows yet a further alternative embodiment of the invention, wherein a spring-loaded element similar to a "toggle bolt" is used within the disc space to hold a mesh screen 1540 or other material over the hole in the annulus. FIG. 15B is a view of the device drawn in FIG. 15A, positioned within the disc.

Figure 16:
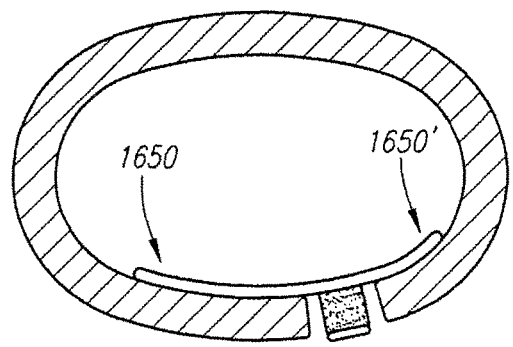
FIG. 16 shows how the arms of the intraspinal component can be asymmetric.

FIG. 16 shows how the arms 1650, 1650' of the intraspinal component may be asymmetric in any of the embodiments. For example, the arm that projects laterally may be shorter than the arm that projects medially. Alternatively, the lateral arm could be curved to accommodate the shape of the disc.

Figure 17A:
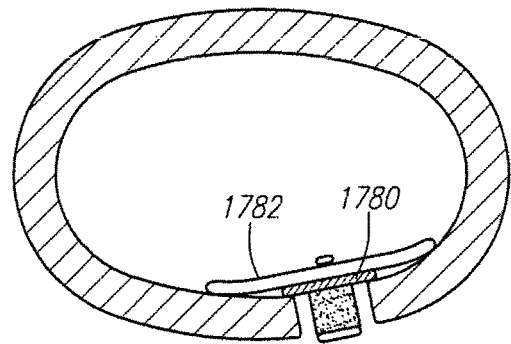
FIG. 17A depicts an optional reinforcing piece behind an intradiscal component.
Figure 17B:
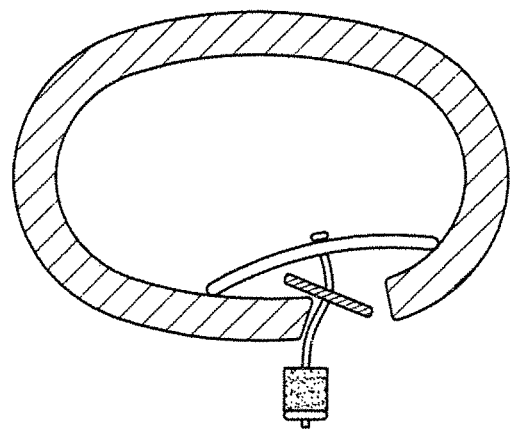
FIG. 17B shows the device of FIG. 17A placed into the disc space.

FIG. 17A is a view of an optional reinforcing piece 1780 behind the intradiscal component 1782. The reinforcing piece 1780 helps prevent bending of the intradiscal component once the device is positioned within disc space. Alternatively, the reinforcing piece could be positioned in front of the intradiscal component with arms. FIG. 17B is a view of the device drawn in FIG. 17A as the device is placed into the disc. The reinforcing piece is positioned first behind the annulus on one side of the hole in the annulus then the behind the annulus on the other side of the hole.

What is claimed:

1. A method for occluding an opening in the annulus fibrosis of an intervertebral disc, the opening having a width and a height, the annulus fibrosis having an outer surface and an inner surface defining an intradiscal space between adjacent vertebrae separated by an intervertebral spacing, the method comprising the steps of:

providing an occluding device having an intradiscal component, an extradiscal component, and a barrier element disposed between the intradiscal component and the extradiscal component;

the intradiscal component comprising first and second arms extending along a first axis and terminating in opposing ends, the opposing ends of the first and second arms defining a first dimension greater than the width of the opening;

the extradiscal component having third and fourth arms extending along a second axis and terminating in with opposing ends, the second axis extending perpendicularly to the first axis, and the opposing ends of the third and fourth arms defining a second dimension greater than the intervertebral spacing; and inserting the intradiscal component and the barrier element through the opening in the annulus fibrosis and into the intradiscal space, with the extradiscal component being positioned adjacent the outer surface of the annulus fibrosis and making a sliding engagement with at least one of the adjacent vertebrae, and with the occluding device being oriented so that the first axis is disposed horizontally across the width of the opening and the second axis is disposed vertically across the height of the opening, and with the first and second arms of the intradiscal component urging the barrier element against the inner wall of the annulus fibrosis adjacent the opening, thereby occluding the opening.

2. The method of claim 1, wherein the first and second arms extend outwardly.

3. The method of claim 1, wherein the first and second arms are connected by a hinge.

4. The method of claim 1, wherein the barrier element is a mesh screen.

5. The method of claim 1, wherein the barrier element is an allograft tendon.

6. The method of claim 1, wherein the barrier element is composed of a resilient or compressible material.

7. The method of claim 1, wherein the barrier element is composed of rubber.

8. The method of claim 1, wherein the occluding device further comprises a biasing element between the intradiscal and extradiscal components, the biasing element being operative to urge the intradiscal and extradiscal components toward one another.

9. The method of claim 8, wherein the biasing element is a spring.

10. The method of claim 8, wherein the biasing element is a tensioning cable.

11. The method of claim 1, wherein the first and second arms are of unequal length.

12. The method of claim 8, wherein the biasing element causes one of the first and second arms and the third and fourth arms to assume a bowed shape, thereby urging the barrier element against the inner wall of the annulus fibrosis adjacent the opening.

* * * * *